(12) United States Patent
Dunlap et al.

(10) Patent No.: US 8,263,526 B2
(45) Date of Patent: Sep. 11, 2012

(54) COMPOSITIONS OF KERATIN HYDROLYSATE AND MICROBES FOR PEST CONTROL APPLICATIONS

(75) Inventors: Christopher A. Dunlap, Dunlap, IL (US); Mark A. Jackson, Peoria, IL (US); Maureen S. Wright, New Orleans, LA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 167 days.

(21) Appl. No.: 12/497,072

(22) Filed: Jul. 2, 2009

(65) Prior Publication Data
US 2009/0269308 A1    Oct. 29, 2009

Related U.S. Application Data (63) Continuation of application No. 11/518,789, filed on Sep. 11, 2006, now abandoned.

(51) Int. Cl.
*A01N 59/00* (2006.01)
(52) U.S. Cl. ............. 504/101; 8/517; 424/406; 530/357
(58) Field of Classification Search ........ 8/517; 424/406; 504/101; 530/357
See application file for complete search history.

(56) References Cited

U.S. PATENT DOCUMENTS

| 5,225,095 | A  | * | 7/1993  | DiMaio et al. ................ 516/14 |
| 5,747,416 | A  |   | 5/1998  | McArdle |
| 6,280,723 | B2 | * | 8/2001  | Stimac et al. ................ 424/93.5 |
| 6,660,291 | B2 | * | 12/2003 | Wright et al. ................ 424/406 |
| 7,033,586 | B2 | * | 4/2006  | Shimizu et al. ............... 424/93.5 |
| 2004/0210039 | A1 |   | 10/2004 | Schrooyen et al. |

OTHER PUBLICATIONS

Sandoval-Coronado, C.F., et al., "Drying and formulation of blastospores of *Paecilomyces fumosoroseus*. . . ", World Journal of Microbiol.& Biotech.,17, pp. 423-428, 2001.

* cited by examiner

*Primary Examiner* — Fereydoun G Sajjadi
*Assistant Examiner* — Ali Soroush
(74) *Attorney, Agent, or Firm* — John Fado; Randall E. Deck; Lesley Shaw (57) ABSTRACT

The combination of keratin hydrolysate with viable cells or infectious propagules of a fungal biological control agent such as *Paecilomyces* species, *Metarhizium* species, *Beauveria* species, and/or *Verticillium* species, provides effective control of soil-dwelling or subterranean insects, including termites, and particularly those belonging to the family Rhinotermitidae, such as the Formosan subterranean termite and native North American subterranean termites. In use, a foam-forming composition comprising the keratin hydrolysate and an insecticidally effective amount of the fungus are applied to the insects, the locus of the insects, to material susceptible to infestation by said insects, or to the locus of material susceptible to infestation by said insects.

35 Claims, 2 Drawing Sheets

COMPOSITIONS OF KERATIN HYDROLYSATE AND MICROBES FOR PEST CONTROL APPLICATIONS

CROSS REFERENCE TO RELATED APPLICATIONS

The present application is a continuation of copending U.S. patent application Ser. No. 11/518,789, filed Sep. 11, 2006, which is hereby incorporated by reference herein in its entirety.

BACKGROUND OF THE INVENTION

1. Field of the Invention

The invention is drawn to compositions and methods effective for controlling termites and soil-dwelling or subterranean insects.

2. Description of the Prior Art

Subterranean termites (ST) are destructive pest insects that destroy cellulosic material such as trees and wood structures. In the United States ST are estimated to cause $1 billion in damage annually, including prevention and repair costs (Su and Scheffrahn, 1990). A predominant species of ST, the Formosan subterranean termite (FST), *Coptotermes formosanus* (Shiraki), has become an economically significant nest in the United States in the past 50 years. This impact is due to the massive size of their colonies which can contain tens of millions of individuals, their propensity to attack several species of living trees, and their high rate of reproduction.

Termite infestations are very difficult to treat due to the cryptic nature of these insects. Formosan termites are even more difficult to control due to the massive numbers of individuals in their colonies and their propensity to attack living trees where nests have been found. Prior to 2005, it was estimated that over 50% of the trees in New Orleans, La. were infested with Formosan subterranean termites. As the Formosan termites consume the heartwood of these trees, the trees are weakened and often fall during strong winds. Formosan termite infestations can also lead to the establishment of carton nests in wooden structures such as homes provided a source of water is available, thus alleviating their need to return to the ground.

The most successful existing methods for control of subterranean termites are preventive rather than remedial. These include barrier treatments to structures and the preemptive treatment of wood materials with chemicals to prevent termite attack. These however have drawbacks. Physical barriers are not compatible for retrofitting on many existing constructions and may not be completely effective, and chemical treatments are only partially effective and last only about five years.

Organochlorine compounds were previously used to control Formosan termites, but their sale was banned in 1988. Replacement chemicals are not as persistent (Su et al., 1998). In addition, by disturbing soil around a structure when landscaping or compensating for soil subsidence the chemical barriers can be compromised and allow termite access to the structure (Su et al., 1990). Su et al. (1998, supra) review some alternative control methods including non-repellant termiticides and bait technology. In order for these techniques to work they must not repel termites, must be easily transferable in or on termite bodies and have delayed toxicity which allows transfer from foraging workers to members of the termite colony that do not forage (Su et al., 1996 and 1998, supra).

Interest in biological insect and fungal control agents is growing as a consequence of concerns regarding chemical pesticide use. The biological control of insect pests presents an alternative means of pest control which can play a role in integrated pest management and reduce dependence on chemical pesticides. Generally, biological agents have little adverse ecological impact due to their specificity for the target host. Also, long term environmental hazards and health concerns are not a factor with biological control agents because chemical residues are not present.

*Paecilomyces fumosoroseus* is an entomopathogenic fungus with potential for use in controlling several insect pests (Osborne, 1990; Altre and Vandenberg, 2001; Vandenberg et al., 2001; Shimizu and Yamaji, 2002). Our laboratories previously identified *P. fumosoroseus* as an effective biological control agent for use in controlling subterranean termites (Wright et al., 2003). Other biological agents, particularly fungi, have also been described for use against termites. Milner et al. (1966) review a wide variety of fungi that have been reported as potential pathogens to termites. Pathogenicity of strains of both *Metarhizium anisopliae* (Metschnikoff) Sorokin and *Beauveria bassiana* (Balsamo) Vuillemin have been demonstrated in laboratory colonies of *C. formosanus* [Delate et al. (1995), Wells et al. (1995), and Jones et al. (1996)] discovered that small numbers of *B. bassiana* and *M. anisopliae* spores can be spread throughout a *C. formosanus* colony without being detected by the termites. Conditions in a termite nest, moderate temperature and high humidity, are conducive to the growth of fungal species and are important factors in fungal survivability and propagation [Kramm et al. (1982), Ignoffo (1992), and Stimac et al.] teach a novel *B. bassiana* strain (ATCC 20872) useful in controlling termites of the genera *Cryptotermes, Coptotermes, Incistermes*, and *Reticulitermes*. The contents of each of above-mentioned publications are hereby incorporated by reference herein.

However, despite these advances, the success of an entomopathogenic biological control agent depends largely on the ability of the agent to be delivered to and establish itself in the insects' environment. The use of microbial agents, such as the blastospores of *P. fumosoroseus*, for controlling Formosan termite infestations, requires that these agents contact the termite, germinate, and infect the termite. Typically, biological control agents are formulated as a wettable powder, wettable granule or liquid suspension (Fravel et al., 1998). While these types of formulations are suitable for most environments, some insects reside in areas difficult to reach, such as the cavities in trees, walls of buildings or subterranean environments. Although the control of insects in trees and walls of buildings is currently accomplished with the application of chemical pesticides in foam formulations, at present, no commercially available foaming agents which are broadly compatible with microbial biological control agents have been described.

SUMMARY OF THE INVENTION

We have now discovered that combining keratin hydrolysate with viable cells or infectious propagules of one or more fungal biological control agents such as *Paecilomyces* species, *Metarhizium* species, *Beauveria* species, and *Verticillium* species provides effective control of a variety of insect pests, particularly soil-dwelling or subterranean insect pests and termites, and most particularly termites belonging to the family Rhinotermitidae, such as the Formosan subterranean termite and native North American subterranean termites. In use, a foam-forming composition comprising the keratin hydrolysate and an insecticidally effective amount of the fungus are applied to the insects, the locus of the insects, to material susceptible to infestation by said insects, or to the locus of material susceptible to infestation by said insects.

In accordance with this discovery, it is an object of this invention to provide improved methods and compositions of fungal biological control agents for controlling soil-dwelling or subterranean insects and termites and protecting wood susceptible to termite damage.

Another object of this invention is to provide improved methods and compositions for controlling termites and soil-dwelling or subterranean insects which exhibit significantly greater efficacy than those using cells of a fungal biological control agent alone.

Yet another object of this invention is to provide improved methods and compositions for controlling soil-dwelling or subterranean insects and termites using a non-biocidal foaming agent compatible with fungal biological control agents such as *P. fumosoroseus*.

A further object of this invention is to provide improved methods and compositions for controlling soil-dwelling or subterranean insects and termites which utilize equipment currently available to commercial pest control workers.

Still another object of this invention is to provide improved methods and compositions for controlling soil-dwelling or subterranean insects and termites utilizing biocompatible foam formulation with physical properties similar to those currently in use with chemical pesticides.

Other objectives and advantages of this invention will become readily apparent from the ensuing description.

DETAILED DESCRIPTION OF THE INVENTION

The compositions of the invention of keratin hydrolysate and fungal biological control agent such as *Paecilomyces* species, *Metarhizium* species, *Beauveria* species, and/or *Verticillium* species, are effective for controlling a variety of insect pests. Insect pests which may be controlled include, but are not limited to subterranean termites, particularly those belonging to the family Rhinotermitidae, such as the Formosan subterranean termite and native North American subterranean termites, and other agronomically important soil-dwelling insects such as Japanese beetles, June beetles, vine weevils, banana weevils, and sugar beet root maggot. As described herein, the term soil-dwelling insects refers to insects which reside or may be typically found under the surface of the soil for at least a portion of their life cycle. Without being limited thereto, we have discovered that formulating the biological control agents with keratin hydrolysate improves biocontrol efficacy by one or more of: acting as a foaming agent with a relatively high expansion ratio (preferably but not limited to approximately 25:1) and delivering the agents to the site of insect activity, providing an exogenous nutrient that increases the rate of germination of blastospores of the agents, improving contact and adhesion of the agents to insect by reducing interfacial water tension, producing a foam which maintains a high water activity around the agents, and providing some native insect control activity. Moreover, we have also discovered that when termites are exposed to the biological control agents in combination with keratin hydrolysate, the termiticidal activity of the agents is synergistically increased. As used herein, a synergist is defined as a first material which enhances the activity of other materials, such as a fungal biological control agent, so that the overall activity of the combination is greater than the sum of the individual materials alone.

In addition to termites, other soil insects such as the grub form of Japanese and June beetles in turf, vine weevils in horticultural plants, the banana weevil in banana plantations, and the sugar beet root maggot in sugar beets, cause serious problems and economic losses in agricultural and urban settings. Although all of these soil-born insect pests can be infected and killed by various entomopathogenic fungi, including *Metarhizium* spp, *Beauveria* spp, *Paecilomyces* spp, and *Verticillium* spp., the delivery of these agents to the target insect is difficult due to their soil habitat. Often these insects feed on plant roots in the top 2-3 inches of soil. Depending on the soil type, drenching with liquid suspensions of biocontrol microorganisms can lead to concentration of the biocontrol microbe in the top 1 inch of soil or percolation of the microbe-containing suspension to soil strata below the target zone. However, the keratin-based foam delivery system of the invention allows the application and retention of the biocontrol fungus to the desired soil strata. The combination of targeted application with the benefits of a nutritive base for fungal growth enhances the efficacy and economics of these agents for insect biocontrol. The keratin-based foam compositions of this invention may also find utility for the application of other fungal biocontrol agents for weed and plant disease control in soil.

Suitable fungal biological control agents for use in the invention are those which are effective for controlling soil-dwelling insects and termites (i.e., causing significant mortality in a population of insects or termites), preferably termites belonging to the family Rhinotermitidae, Japanese beetles, June beetles, vine weevils, banana weevils, and sugar beet root maggots, and most preferably the Formosan subterranean termite (*Coptotermes formosanus*) and native North American subterranean termites (*Reticulitermes flavipes*). Other target Rhinotermitidae species of potential economic interest include *R. hesperus*, and *R. virginicus*. Preferred fungal biological control agents include, but are not limited to, one or more of *Paecilomyces* species, *Metarhizium* species, *Beauveria* species, and *Verticillium* species, although *Metarhizium anisopliae*, *Beauveria bassiana*, and most particularly, *Paecilomyces* species, are preferred. More preferred *Paecilomyces* species include a variety of strains of *P. fumosoroseus* or closely-related species, such as *P. javanicus*, such as described by Wright et al. (U.S. Pat. No. 6,660,291, the contents of which are incorporated by reference herein). Exemplary strains of *P. fumosoroseus*, without limitation thereto, include ARSEF 4480, ARSEF 3531, ARSEF 3878, ARSEF 4489, ARSEF 4491, and ATCC 20874. An exemplary strain of *P. javanicus* is ARSEF 322. ARSEF accessions are freely available from the U.S. Department of Agriculture, Agricultural Research Service Entomopathogenic Fungus collection, Tower Road, Ithaca, N.Y. 14853-2901.

The preferred cells or propagules of interest are spores (i.e., blastospores), and particularly dessication tolerant blastospores as described by Jackson in U.S. Pat. No. 5,968,808, the contents of which are incorporated by reference herein. The blastospores described by Jackson are produced in a liquid culture medium. Also contemplated by the invention are control agents comprising blastospores in combination with conidia and/or mycelia. These may be applied to the treatment area in the form of a recovered culture broth or in combination with a suitable vehicle or carrier that does not substantially interfere with the viability of the fungus. However, blastospores of *P. fumosoroseus* are particularly preferred for use with foam formulations since these blastospores have been shown to have excellent insecticidal efficacy against several insect species (Fargues et al., 1994; Jackson et al., 1997; Vandenberg et al., 1998; Vega et al., 1999) and can be economically produced using deep tank fermentation (Jackson et al., 2003).

Keratin hydrolysate suitable for use herein is widely available commercially, such as that used in firefighting foams, and a variety of techniques for its production are also known. For use in this invention, the particular source of the keratin hydrolysate and/or its manner of production is not critical. For instance, without being limited thereto, hydrolyzed keratin protein may be produced by hydrolysis of animal hooves and horns, fish scales, hair, wool, animal bristles, or feathers. These keratinaceous materials may be hydrolyzed by acid or alkaline chemical hydrolysis, or by enzymatic digestion, into peptides, polypeptides, and amino acids and their salts, by a variety of known techniques. Non-limiting examples of these techniques include alkaline hydrolysis with lime or NaOH such as described by DiMaio et al., acid hydrolysis such as described by Dupuis et al., and enzymatic hydrolysis such as described by Keil and Ingraham, or Savolainen, or any of these techniques such as described by Matsunaga et al., wherein the contents of each of the above-mentioned patents are incorporated by reference herein. Typically, use of dry, powdered keratin hydrolysate is preferred [preferably mixed in a 40% (w/w) solution] because most commercially available keratin hydrolysate is sold in this form. In an optional embodiment, to minimize or eliminate the presence of any compounds or microorganisms which might act as a deterrent to the target insects, and particularly termites (or which microorganisms might produce an extracellular product which may function as a deterrent), the keratin hydrolysate is preferably substantially pure. The keratin hydrolysate may also be treated to kill substantially all viable, non-spore-forming microorganisms, preferably at least about 99.9% therein, such as by using sterilization techniques known the art.

Formulations of the fungal biological control agent and hydrolyzed keratin may be in liquid or dried form, including solutions, emulsions, concentrates, powders or granules. If the formulations are to be prepared and stored prior to use, dry formulations are generally preferred. As a practical, it is envisioned that at the time of application or shortly before, the compositions will be formulated with a suitable liquid inert carrier or diluent as is known in the art, preferably water, to facilitate delivery and subsequent foam formation. Not only is water a preferred carrier for the keratin hydrolysate foam forming agent, but subterranean termites are normally attracted to and reliant upon the presence of moisture, rendering its use more advantageous. However, it is understood that other carriers may be suitable for use herein, such as alcohols, ethers, glycols, ketones, esters. The concentration of the keratin hydrolysate is not critical and may be readily determined by the skilled practitioner, but should be effective to generate a foam when applied. Without being limited thereto, suitable concentrations of keratin hydrolysate, measured in the foam forming composition including the carrier, is between about 0.1% to about 10%, preferably between about 1 to about 2% (w/w) optimal.

The amount of the fungal biological control agent is selected to provide a concentration in the foam which is effective for control of insects, i.e., an insecticidally effective amount. Thus, when the object of the invention is the control of termites, the fungal biological control agent is applied in a termiticidally effective amount. As used herein, the term "insecticide" (or "termiticide") refers to a material or mixture of materials which induce mortality, disrupt or impede growth, interfere with metamorphosis or other morphogenic functions, effect sterilization, or interfere with reproduction of the targeted insects (or termites). The term "controlling" is used herein to mean that the population is reduced, principally through mortality, at a level that is significantly greater than an untreated control population. "Significant mortality" is defined herein to mean that the percentage of insects that die within a given period of time after coming into contact with the insecticide is significantly greater than the number of insects that have not come in contact with the insecticide that die during the same period of time. An "effective amount" is therefore used herein in reference to that quantity of Fungal biological control agent necessary to obtain significant mortality in a population or colony of insects compared to an untreated control group (measured at a confidence level of at least 95%). The actual amount of agent needed for a particular application will be dependent upon a number of factors, such as the environmental conditions, the particular fungal strain being used, the species of target insect, and the composition of the formulation. The person of ordinary skill in the art would be able to experimentally determine an actual effective amount for a particular situation by observing the success of a control regimen, and then modifying it accordingly. Without being limited thereto, we have found that suitable concentrations of cells or propagules in the foam-forming composition (including carrier) are between about $1\times10^3$ and about $1\times10^{12}$ cfu/ml, with a concentration between about $1\times10^8$ and about $1\times10^9$ cfu/ml being preferred.

A variety of other optional components may be included in the formulation. For instance, preferred adjuvants include foam stabilizers and viscosity modifiers, such as polyvalent metal ion salts (salts of $Fe^{2+}$, $Ca^{2+}$ and $Zn^{2+}$), which stabilize the foam through cross-linking keratin peptides or added anionic polymers through ionic interactions. Viscosity modifiers such as gums, polysaccharides, starches and synthetic polymers may also be included, as well as dispersants such as, ligno-sulfate, diatomaceous earth, clays, and deliquescents for control of foam lifetime. Humectants, such as sorbitol, dulcitol, lactic acid, mannitol and other polyols, which control water activity may be added for foam stability and/or preferential microbial growth and stability. Growth of the fungal biological control agents following application may be enhanced by addition of nutritive or probiotic amendments such as minerals, vitamins, carbon sources and/or other nitrogen sources. Antimicrobials which prevent bacterial/fungal contamination, while permitting survival of the delivered microbe may be provided as well. Conversely, the composition should be substantially free of antifungal or antimicrobial agents effective against the fungal biological control agents (i.e., lacking antifungal or antimicrobial agents in an amount effective to substantially inhibit the efficacy of the fungus as a termiticide).

Further adjuvants which may be included include secondary agents having insecticidal activity (or termiticidal activity when the target insect is a termite) or agents which increase the attractancy of termites or other insects to the composition (or reduce repellancy). Suitable secondary insecticides and termiticides include, but are not limited to, biological controls such as insect growth regulators, and materials or organisms that are toxic to insects (i.e., toxicants) such as chemical insecticides, pathogenic nematodes, other fungi, protozoans, viruses, or bacteria. Preferred secondary termiticides are slow-acting (i.e., killing exposed termites after hours, days or weeks), to reduce "avoidance" effects before individuals have infected other members of the colony with the fungal biological control agents. A variety of slow-acting termiticides are known in the art, and include, for example silafluofen, borates (boric acid, disodium octaborate tetrahydrate), sulfluramid and other fluoroalkyl sulfonamides, avermectin, hydramethylnon, hexaflumuron and other chitin synthesis inhibitors and other acyl ureas, diflubenzuron (Dimilin), azadirachtin, dechlorane (Mirex), diiodomethyl-para-tolyl sulfone (A-9248), fluorosulfonates, imidacloprid, azadirachtin, cyromazine, juvenile hormones and juvenile hormone mimics or analogs such as fenoxycarb, methoprene, hydroprene, triprene, furnesinic acid ethyl and alkoxy derivatives, and pyriproxyfen (Nylar), and the plant *Rheuneo jupanic* Thunb. Roth. The mortality rate of otherwise faster-acting insecticides may be retarded by microencapsulation or other slow-release formulation. Biological control agents that may be used as secondary termiticides include *Aspergillus flavus*, nematodes such as *Neoplectana carpocapsae*, insect viruses such as granulovirus, nuclear polyhedrosis virus, pathogenic bacteria such as *Bacillus thuringiensis* and *Serratia marcescens*, and toxins derived from biological control agents such as *B. thuringiensis* toxin.

Still further optional adjuvants include insect attractants such as pheromones of the target insects, or target insect extracts containing pheromones or pheromone mimics. Termite pheromones suitable for use herein are generally well-known in the art, and include, for example, (Z,Z,E)-3,6,8-dodecatrien-1-ol, and the aggregation pheromone-hexanoic acid. The composition may also include one or more additional insect attractants such as food odor attractants or aggregation attractants, or phagostimulants which lure the pest to the control agent or remain in the treated area. Without being limited thereto, suitable food odor attractants are described by Peterson (U.S. Pat. No. 5,756,114), the contents of which are incorporated by reference herein. It is also envisioned that termite or insect repellents and phagodeterrents, which provide for residual control may be included. Gases, either inhibitory to termites or beneficial to the fungal biological control agent, may be included as well.

In use, a foam-forming composition of the keratin hydrolysate and an insecticidally effective amount of the fungus are applied directly to the insects, the locus of the insects, to material susceptible to infestation by the insects, or to the locus of material susceptible to infestation by the insects. Treatment areas for termites may include woody environments such as lumber, structures or buildings constructed at least in part from wood, dead or living plants, particularly trees, forests, orchards or other agricultural fields which are subject to termite attack. Treatment areas for other insects may also include gardens, orchards, nurseries, greenhouses or agricultural crop fields. The foam-forming composition may be applied to loci infested with insects, or which may be potentially infested. The delivery of the composition and generation of the foam may be effected using conventional techniques in the art. For example, without being limited thereto, application is preferably effected by spraying or pumping the composition into the desired treatment area. The foam may be generated, for example, by agitating, whipping, shaking the composition in the presence of air or inert gas, or by injecting or sparging the air or gas into the composition. Air or other gases such as, carbon dioxide, carbon monoxide, nitrogen, which are injurious to the target insect or beneficial to the delivered microbe, are preferred.

The following Examples are intended only to further illustrate the invention and are not intended to limit the scope of the invention, which is defined by the claims.

EXAMPLE 1

Several classes of surfactants/foaming agents were screened for compatibility with blastospores of *Paecilomyces fumosoroseus*. The surfactants were assayed to determine their influence on the rate of germination, viability and conidia production by blastospores of *P. fumosoroseus*. Compatible surfactants were then assayed for their foam forming properties using a commercially available foam generator. These tests identified keratin hydrolysate as the only suitable surfactant in terms of biocompatibility and foam forming properties. Laboratory assays were conducted to determine the effect of keratin hydrolysate on the efficacy of blastospores of *P. fumosoroseus* against Formosan subterranean termites. The results show keratin hydrolysate increased the efficacy of *P. fumosoroseus*. A preliminary field trial was performed to test the ability of a *P. fumosoroseus* foam formulation to control Formosan subterranean termites in infested trees. The results show this foam formulation of *P. fumosoroseus* is successful in controlling Formosan subterranean termites.

Materials

Egg albumen was provided by Ballas Egg Products Corporation (Zanesville, Ohio). Whey protein isolate was provided by Glanbia Nutritionals (Monroe, Wis.). Sodium caseinate was provided by the Milky Whey Corporation (Missoula, Mont.). Sodium lauryl hydrolyzed silk protein (Promois EFLS) was provided by Rita Corporation (Crystal Lake, Ill.). Hydrolyzed keratin (alkaline hydrolyzed) was provided by Kidde Fire Fighting Corporation (Exton, Pa.). The detergents were obtained from Pilot Chemical Corporation (Santa Fe Springs, Calif.), under the tradenames CALFOAM ES-702 (sodium lauryl ether sulfate (2-mole)) and CAL-SOFT AOS-40 (sodium alpha olefin sulfonate) and L-60 (sodium linear alkyl benzene sulfonate). TWEEN 20, TRITON X-100 and hexadecyl trimethylammonium bromide were obtained from Sigma-Aldrich (St Louis, Mo.) in analytical grade or the highest grade available. Foam was produced using a commercial foam generator (PF-6 Pestifoamer, Richway Industries, Janesville, Iowa). Chemicals not specifically mentioned were obtained from Sigma-Aldrich (St Louis, Mo.) in analytical grade or the highest grade available. Aqueous solutions of 40% keratin hydrolysate were sterilized by autoclaving for 20 minutes.

Preparation of Blastospores of *P. fumosoroseus*

Blastospores of *P. fumosoroseus* were produced in submerged liquid culture using a previously described methodology (Jackson et al., 2003) and air-dried with diatomaceous earth as previously described (Jackson et al., 1997). Blastospore suspensions ($\sim 1\times 10^8$ blastospores/ml) were prepared by adding 1.3 g of the dried blastospores of *P. fumosoroseus* formulate to 100 ml sterile deionized water. The spore suspension was stirred for 30 minutes, and then allowed to stand 1 minute to allow the diatomaceous earth to settle. Without disturbing the diatomaceous earth, 30 ml of the spore suspension was removed and transferred to a sterile bottle. The blastospore concentration of the suspension was measured using a hemacytometer.

% Germination Assay

A one ml aliquot of the previously described blastospore suspension was added to 49 ml of the foaming agents in a 250 ml baffled Erlenmeyer flask. The blastospore suspensions were incubated in a rotary shaker incubator (Innova 4000, New Brunswick) at 300 RPM and 28° C. for 6 hours. Blastospore germination was measured by microscopic observation of the germ tube formation. Four slides were prepared from the incubated blastospore suspension using separate pipets. Germ tube formation was measured for 100 blastospores on each slide. A total of 400 blastospores were counted from each flask.

Viability and Conidia Production Assays

For these studies, 1 ml of the previously described blastospore suspension was added to 49 ml of the foaming agents and held for 1 hour at room temperature. After the one hour exposure period, colony forming units (cfu) were determined for blastospore suspensions using standard spread plating techniques. Appropriate dilutions of blastospore suspensions were spread on SDMA (Sabouraud dextrose maltose agar) plates, 10 g Bacto peptone, 20 g Difco dextrose, 20 g Sigma maltose, and 15 g Bacto agar per 1 L water. Three plates were used for each dilution. Plates were incubated at 28° C. for 2-3 days and CFUs counted.

For the conidia production assay, 100 ul of the blastospore suspension was spread onto WA plates (Water Agar: 20 g/L water.) and incubated 2 weeks in the dark. Three plates were used for each treatment. The drop was spread with a sterile plastic spreader and incubated at 23° C. in the dark for 2 weeks. After two weeks, 5 ml of sterile water was added to each plate, and a sterile loop was used to release the conidia from the fungal growth. The spore suspension was drawn up with a pipet and the volume measured. The conidia concentration was measured using a hemacytometer. Our previous determination of the blastospore concentration in the suspension applied to the SDMA plates was used to calculate conidia production/blastospore.

The viability of blastospores of $P.\ fumosoroseus$ before and after the foaming process was measured as cfus using the spread plate method as described above. In addition, blastospore cfus were measured immediately after foaming and after the foam collapse.

Foam Characterization

Foam characterization was performed using a modified method, based on standard techniques (Phillips et al., 1990). A 2000 ml polypropylene graduated cylinder was modified by drilling two 6 mm holes in the bottom on opposite sides. The holes were covered with tape and the cylinder's weight determined. Foam was produced using a commercial foam generator charged with various foam-producing solutions. Foam was discarded until uniform foam was produced. The foam was then collected in the cylinder and its weight and volume determined. The seal on the tape was broken and the liquid draining from the foam was collected over a balance until 50% of the initial foam mass was recovered and the time was recorded. This time is the drainage hall-life for the foam. The expansion index of the foam is the volume of foam generated divided by its mass. Three or more replicates were performed for each foam preparation.

Formosan Termite Bioassays

For laboratory bioassays, Formosan subterranean termite workers, third instar or older based on size, and soldiers were obtained from bucket traps (Su and Scheffrahn, 1986) set up at City Park, and the University of New Orleans, both of which are located in New Orleans, La. Formosan subterranean termite workers from four different termite colonies were chosen for these assays to prevent colony vitality biasing of data.

Bioassays were conducted to evaluate the impact of exposing FST to keratin hydrolysates in the presence or absence of blastospores of $P.\ fumosoroseus$. Whatman filter discs (90 mm) were placed in the lid of a Petri dish (100×15 mm) and moistened with either 1 ml of deionized water or 1 ml of various keratin solutions. The various keratin solutions tested included 1% sterile, 1% unsterile, 2% sterile and 2% unsterile keratin. To evaluate the impact of the keratin hydrolysates on the biocontrol efficacy of blastospores of $P.\ fumosoroseus$, 10 Formosan subterranean termites (9 workers and 1 soldier) were allowed to walk for 5 minutes on 2 g of a dried, $P.\ fumosoroseus$ blastospore formulation containing $9.3 \times 10^9$ spores/g. These 10 Formosan subterranean termites were removed from the blastospore formulation and placed with 10 unexposed Formosan subterranean nestmates (9 workers and 1 soldier) in the Petri plates containing filter discs moistened with the various keratin hydrolysates or water. The FST were kept in these Petri plates at 25° C. and 95% humidity in an incubator. Termite mortality was monitored daily for 28 days.

Bioassay data were analyzed using analysis of variance (ANOVA) and least significant difference (LSD) at P? 0.05 (Cody and Smith, 1997). In each experiment, treatments with the same letter on the same day are not significantly different. All analyses were run using the SAS System Software (Cody and Smith, 1997).

Formosan Subterranean Termite Field Trial

Five trees (water & red oak) were located City Park, New Orleans, La. that were infested with Formosan subterranean termites. Formosan subterranean termite infested trees were identified by drilling a minimum of eight holes into the base of a tree and inserting a video probe (Everest VIT PXL-620A) to visually identify termite activity. Foam containing 2% keratin and $4 \times 10^8$ blastospores/ml of $P.\ fumosoroseus$ was then injected into the tree through drill holes using the previously described commercial foam generator (PF-6 Pestifoamer, Richway Industries, Janesville, Iowa). Foam was injected into the trees until it was visible from cracks or holes in the tree or until 5 liquid gallons of foam solution was injected. The blastospore suspension and keratin hydrolysate were diluted to final concentration and mixed together in the tank of the foam generator immediately before injection into the tree. Termite activity was assessed initially and over time by using the fiber optic camera to revisit the same drill holes for visual observation of termite activity.

Results & Discussion

Compatibility of Surfactants with $P.\ fumosoroseus$

Several classes of surfactants were screened for their compatibility with blastospores of $P.\ fumosoroseus$ by evaluating blastospore germination, colony forming capability and conidia production capability after exposure to the foaming agent. Surfactants were chosen for screening based on their ability to produce foams with the desired characteristics (expansion ratio and drainage half life). The surfactants tested can be divided into 3 classes; proteins, protein hydrolysates and small molecules. The small molecule surfactants can be further subdivided based on their ionic nature; anionic, cationic, or nonionic. Current commercial chemical foam pesticide formulations typically use anionic linear alkyl sulfonates for foaming agents. The results of the blastospore compatibility assays are compiled in Table 1. The germination assay results show all the protein based surfactants tested increased the germination rate of blastospores of $P.\ fumosoroseus$ under these conditions relative to the water-only control. The sodium lauryl hydrolyzed silk protein and all the small molecule surfactants decreased or prevented entirely the germination of the blastospores. Interestingly, the two nonionic surfactants TWEEN 20 and TRITON X-100 were the only small molecules to allow germination under these conditions, albeit strongly inhibited. The anionic and cationic small molecule surfactants were excluded from further assays since they prevented or delayed the germination of blastospores of *P. fumosoroseus*. The rapid germination of blastospores is considered critical for consistent biocontrol efficacy of contact biopesticides like *P. fumosoroseus* (Vega et al., 1999).

The colony forming unit assay measured the ability of blastospores of *P. fumosoroseus* to recover from and germinate after exposure to the surfactants. The results show only the sodium lauryl hydrolyzed silk protein at 0.5% concentration inhibited cfu formation. The two nonionic surfactants Tween 20 and Triton x-100 had comparable or better cfu formation than the water control. There are several possibilities to explain the differences in viability observed for these small molecules in these two assays; i) the surfactants do not kill the blastospore and only retard their germination, ii) the plating dilutes the surfactant to a non-lethal concentration, iii) the surfactant enhances the dispersion of the blastospores during plating. The proteins and keratin hydrolysate all had comparable or greater cfu formation relative to the water control. These results would be expected based on the 6 hour germination assay.

The conidia production assay measured the impact of the surfactants on the ability of blastospores of *P. fumosoroseus* to germinate, grow and sporulate on nutrient-poor water agar in the dark, conditions that somewhat mimic those found in termite galleries within trees. The results showed that all the surfactants tested, except Triton x-100, had comparable or better conidia production relative to the water control. Many of the proteins and protein hydrolysates tested exhibited significant increases in conidia production under these conditions. This is most likely due to the added nitrogen present in the protein-based surfactants. It is envisioned that the ability of *P. fumosoroseus* cultures to sporulate in the dark and their increased spore production when protein-based foaming agents are used may result in enhanced biocontrol efficacy against FST by increasing the number of infective propagules in the FST environment and creating an environment that is unattractive to the FST.

Foaming Properties of Compatible Surfactants

Surfactants that demonstrated *P. fumosoroseus* compatibility in the germination and viability assays were further screened for their foam forming properties. A commercially available foam generator (Pestifoamer) was used to test the foaming properties of the previously screened proteins and protein hydrolysate. Two percent solutions of the proteins and 1 and 2% solutions of the keratin hydrolysate were tested to determine their foam expansion ratio and foam drainage half-life. The results are summarized in Table 2. The results show that keratin hydrolysate exhibited the highest foaming expansion ratio and foam half life. Both the egg albumen and sodium caseinate produced poor foam under these conditions. It is unclear why these proteins produced poor foams with the Pestifoamer, since their established foaming properties are well documented (Phillips et al., 1990; Rodriguez Patino et al., 1995; Baniel et al., 1997; Slattery and Fitzgerald, 1998). It is also known that foam forming processes can greatly effect foam properties (Bisperink et al., 1992). Foams have been produced using whipping, injection, sparging and shaking to incorporate gas into a solution (Bickerman, 1973). The Pestifoamer utilizes a sparging technique to generate foam. These results show keratin hydrolysate based foams can provide the same performance properties of current commercial termiticidal foams. Typically, chemical pesticide foams are applied with an expansion ratio of 20:1 to 30:1.

Since keratin hydrolysate was the only compatible surfactant with suitable foaming properties, it was further tested for additional properties. Keratin hydrolysate is currently commercially available for use as a fire fighting foam and is formulated with a biocide to improve shelf life. The ability to sterilize keratin hydrolysate without a biocide would be essential for use in a microbial biocontrol application. A 40% aqueous solution of keratin hydrolysate was autoclaved and after dilution its foaming properties were tested. The results in Table 2 show autoclaving had no significant effect on its foaming properties. The foaming properties were also tested after the addition of blastospores of *P. fumosoroseus* at the anticipated application rate ($4 \times 10^8$ blastospores/ml). The presence of the blastospores decreased the expansion ratio of the foam produced and had only a minor effect on the drainage half-life. In addition, the viability (cfu/spread plate assay) of the blastospores of *P. fumosoroseus* was assayed before and after the foaming process. The foaming process had no effect on the viability of blastospores of *P. fumosoroseus* (data not shown).

Laboratory Bioactivity Assays

The effect of keratin hydrolysate on efficacy of blastospores of *P. fumosoroseus* against Formosan subterranean termites was assayed with laboratory bioactivity assays. In addition, the effect of autoclaving the keratin hydrolysate was examined. The results for autoclaved keratin are reported in FIG. 1. The results show keratin hydrolysate significantly increased the efficacy of blastospores of *P. fumosoroseus* at days 7 and 14. Interestingly, the keratin hydrolysate alone exhibited some activity against the termites. The nature of this activity is unclear. The keratin hydrolysate may be toxic to the termites or may act as a stimulant for microbial pathogens already present on the termites. The results for non-autoclaved keratin hydrolysate are reported in FIG. 2. The results show a different effect from that of the autoclaved keratin hydrolysate. Autoclaved keratin shows an increase in efficacy going from 1% to 2%, while the non-autoclaved keratin hydrolysate shows a decrease in efficacy going from 1% to 2% keratin. This suggests the non-sterile keratin hydrolysate may have a microbial contaminant that inhibits the efficacy of blastospores of *P. fumosoroseus*.

Figure 1:
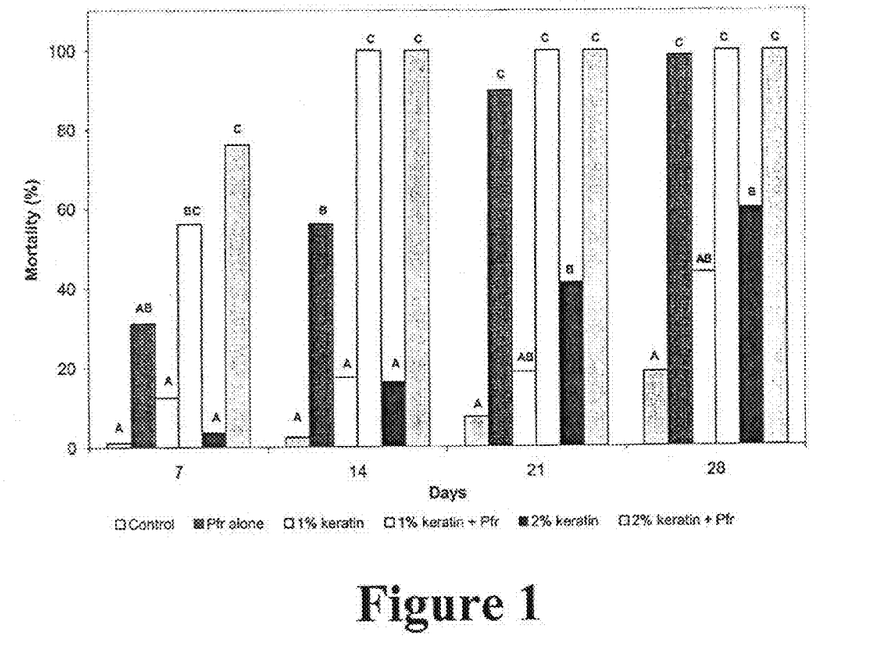
FIG. 1 shows the effect of autoclaved keratin hydrolysate on the efficacy of blastospores of *P. fumosoroseus* (Pfr) against Formosan subterranean termites. Mean values for a given day followed by different letters are significantly different using LSD ($P<0.05$).
Figure 2:
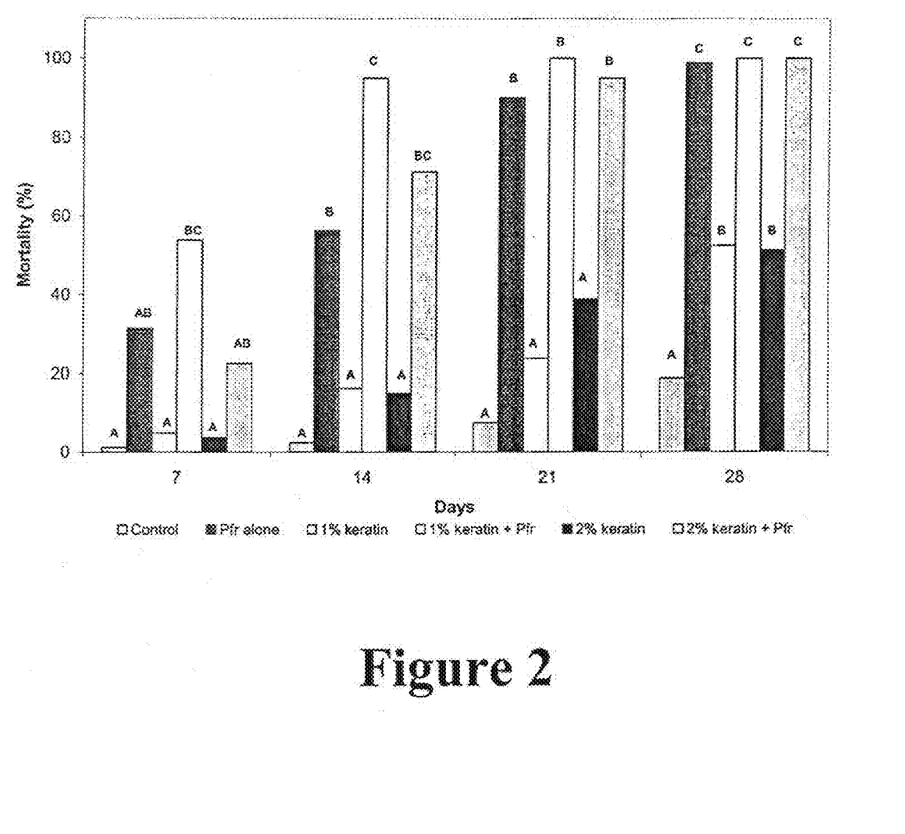
FIG. 2 shows the effect of non-autoclaved keratin hydrolysate on the efficacy of blastospores of *P. fumosoroseus* (Pfr) against Formosan subterranean termites. Mean values for a given day followed by different letters are significantly different using LSD ($P<0.05$).

Keratin hydrolysate may increase the efficacy of blastospores of *P. fumosoroseus* against Formosan subterranean termites through a number of mechanisms. Keratin hydrolysate increased the rate of germination of blastospores of *P. fumosoroseus* as earlier demonstrated. This may allow the blastospores of *P. fumosoroseus* to be more likely to infect the termites before the termites remove them through grooming habits. Keratin hydrolysate increased the conidia production in assays. This would provide a greater number of infective propagules, which could lead to higher efficacy. In addition, the surface active properties of keratin hydrolysate may be responsible for the increase in efficacy. The keratin hydrolysate may disperse the blastospores of *P. fumosoroseus* better and increase the number of "effective" blastospores. The reduction in surface tension could also promote better adhesion to the termite by lowering the interfacial surface energy at the point of contact.

Field Trials for Bioactivity

To further determine the efficacy of blastospores of *P. fumosoroseus* formulated as keratin hydrolysate foam, a preliminary field trial was performed. The results are reported in Table 3. The *P. fumosoroseus* foam formulation was successful in controlling Formosan subterranean termites under these conditions. While termite activity was primarily determined through visual observations, the treated trees showed signs consistent with termite control. For example, termites did not fill the drill holes with mud in treated trees. Visual observations with the video probe showed the presence of termite cadavers and insect that feed on cadavers (carpenter ants and Dipteran larvae). These observations showed the presence of other insects such as springtails, earwigs, and cockroaches which are not normally found around active Formosan subterranean termite colonies. The only treatment failure occurred while treating an exceptionally large Water Oak tree. Better control may have been achieved with a larger initial volume of foam. We limited this treatment to five liquid gallons of foam solution and there were no signs the tree or cavities within the tree were saturated with foam. A control tree treated with keratin hydrolysate foam only still showed heavy Formosan subterranean termite activity during subsequent observations. These results reinforce the positive results observed in the laboratory assays and demonstrate the potential of a microbial biological control foam formulation for controlling Formosan subterranean termites.

It is understood that the foregoing detailed description is given merely by way of illustration and that modifications and variations may be made therein without departing from the spirit and scope of the invention.

TABLE 1

The influence of surfactants on blastospores of *Paecilomyces fumosoroseus* ARSEF 3581.

|  | concentration (w/w) | % viability 6-hr germination | % viability CFU, spread plate assay | *conidia* production (*conidia*/blastospore) |
|---|---|---|---|---|
| Egg albumen | 0.5% | 92.8 a* | 49.6 b | 321 d, e, f |
|  | 1.0% | 92.1 a | 50.6 b | 378 d, e, f |
|  | 2.0% | 88.4 a | 48.4 b | 437 d, e |
| β-casein | 0.5% | 91.3 a | 65.2 a, b | 418 d, e |
|  | 1.0% | 89.9 a | 67.0 a, b | 667 a, b |
|  | 2.0% | 90.3 a | 62.0 a, b | 826 a |
| Whey protein isolate | 0.5% | 88.3 a | 50.1 b | 363 d, e, f |
|  | 1.0% | 88.7 a | 55.7 a, b | 488 c, d |
|  | 2.0% | 86.2 a | 57.4 a, b | 621 b, c |
| Keratin hydrolysate | 0.5% | 87.2 a | 52.0 a, b | 266 e, f, g |
|  | 1.0% | 86.7 a | 42.8 a | 282 e, f |
|  | 2.0% | 88.0 a | 43.6 a | 341 e, f |
| Na lauryl hydrolyzed silk protein | 0.5% | 0.4 e | 4.5 c | 337 d, e, f |
|  | 1.0% | 0.0 e | 45.2 b | 382 d, e, f |
|  | 2.0% | 0.0 e | 64.5 a, b | 353 d, e, f |
| Tween 20 | 0.5% | 12.1 d, e | 47.9 b | 265 e, f, g |
|  | 1.0% | 23..2 c, d | 50.0 b | 268 e, f, g |
|  | 2.0% | 24.5 c, d | 54.1 a, b | 279 e, f |
| Triton x-100 | 0.5% | 12.1 d, e | 52.4 a, b | 95 g, h |
|  | 1.0% | 10.4 d, e | 57.4 a, b | 57 h |
|  | 2.0% | 10.4 d, e | 76.1 a | 27 h |
| Na Lauryl ether sulfate (2-mole) | 0.5% | 0.0 e | not tested | not tested |
|  | 1.0% | 0.0 e | not tested | not tested |
|  | 2.0% | 0.0 e | not tested | not tested |
| Na linear alkyl benzene sulfonate | 0.5% | 0.0 e | not tested | not tested |
|  | 1.0% | 0.0 e | not tested | not tested |
|  | 2.0% | 0.0 e | not tested | not tested |
| Na alpha olefin sulfonate | 0.5% | 0.0 e | not tested | not tested |
|  | 1.0% | 0.0 e | not tested | not tested |
|  | 2.0% | 0.0 e | not tested | not tested |
| hexadecyl trimethylammonium Br | 0.5% | 0.0 e | not tested | not tested |
| Control—water |  | 63.6 b | 41.8 b | 236 f, g |

*Mean values in columns followed by different letters are significantly different using Tukey-Kramer HSD ($P < 0.05$).

TABLE 2

Foaming properties of compatible surfactants.

| Sample | concentration (w/w) | Expansion index | Drainage half-life (min) |
|---|---|---|---|
| Egg albumen | 2.0% | <2 | n/a |
| β-casein | 2.0% | <2 | n/a |
| Whey protein isolate | 2.0% | 8.3 ± 0.4 | 14.3 ± 1.2 |
| Keratin hydrolysate | 1.0% | 22.2 ± 0.6 | 29.7 ± 2.5 |
|  | 2.0% | 28.0 ± 0.8 | 28.8 ± 2.8 |
| Autoclaved keratin hydrolysate | 1.0% | 21.4 ± 0.4 | 25.9 ± 2.8 |
|  | 2.0% | 28.9 ± 0.7 | 29.6 ± 3.2 |
| Keratin hydrolysate with *P. fumosoroseus* | 1.0% | 18.3 ± 0.4 | 23.2 ± 2.7 |
|  | 2.0% | 21.2 ± 0.8 | 26.5 ± 3.2 |

TABLE 3

Field test with keratin hydroysate and blastospores of *Paecilomyces fumosoroseus* ARSEF 3581.

| Tree Number | Type | Treatment | Termite activity | | | | |
|---|---|---|---|---|---|---|---|
| | | | day 0 | day 9 | day 38 | day 52 | day 100 |
| 1 | Red Oak | 4 gallons (no Pfr) | ++++ | ++++ | ++++ | ++++ | ++++ |
| 2 | Red Oak | 5 gallons w/ Pfr | ++++ | $+^a$ | $-^{a,c}$ | $-^a$ | $-^c$ |
| 3 | Red Oak | 4 gallons w/ Pfr | ++++ | $-^{a,b,c}$ | $-^c$ | $-^c$ | $-^c$ |
| 4 | Water Oak | 5 gallons w/ Pfr | ++++ | $-^c$ | $-^c$ | $-^c$ | $-^c$ |
| 5 | Water Oak | 5 gallons w/ Pfr | ++++ | $+^a$ | ++ | +++ | ++++ |

The trees were treated with foam containing 2% keratin hydrolysate and $4 \times 10^8$ ml$^{-1}$ blastospores of *P. fumosoroseus*. Termite activity is subjectively defined as; ++++ heavy infestation, +++ moderate infestation, ++ small groups of termites observed, + only individual termite sightings. Notes: a.) Fungal growth observed. b) Dipteran larvae present (known to feed on FST cadavers), c) Carpenter ants present (known to feed on FST cadavers).

References

Altre, J. A., and Vandenberg, J. D. (2001) Factors influencing the infectivity of isolates of *Paecilomyces fumosoroseus* against diamondback moth, *Plutella xylostella*. J. Invertebr. Pathol. 78, 31-36.

Baniel, A., Fains, A., and Popineau, Y. (1997) Foaming properties of egg albumen with a bubbling apparatus compared with whipping. J. Food Sci., 377-381.

Bickerman, J. J. (1973) Foams. New York: Springer-Verlag.

Bisperink, C. G. J., Ronteltap, A. D., and Prins, A. (1992) Bubble-size distributions in foams. Adv Colloid Interface Sci 38, 13-32.

Cody, R. P., and Smith, J. K. (1997) Applied Statistics and the SAS Programming Language. NJ: Prentice-Hall, Inc.

Delate et al. (1995) J. Appl. Entomol. 119, 429-433.

DiMaio et al., U.S. Pat. No. 5,225,095.

Dupuis et al., U.S. Pat. No. 5,679,329.

Fargues, J., Maniania, N., and Delmas, J. C. (1994) Infectivity of propagules of *Paecilomyces fumosoroseus* during in vitro development to *Spodoptera frugiperda*. J. Invertebr. Pathol. 64, 173-178.

Fravel, D. R., Connick Jr, W. J., and Lewis, J. A. (1998) Formulation of microorganisms to control plant diseases. In Formulation of microbial biopesticides: beneficial microorganisms, nematodes and seed treatments. Burges, H. D. (ed). Dordrecht: Kluwer Academic publishers.

Ignoffo (1992) Florida Entomol. 75, 516-525.

Jackson, M. A., Cliquet, S., and Iten, L. B. (2003) Media and fermentation processes for the rapid production of high concentrations of stable blastospores of the bioinsecticidal fungus *Paecilomyces fumosoroseus*. Biocontrol Sci. Technol. 13, 23-33.

Jackson, M. A., Mcguire, M. R., Lacey, L. A., and Wraight, S. P. (1997) Liquid culture production of desiccation tolerant blastospores of the bioinsecticidal fungus *Paecilomyces fumosoroseus*. Mycol. Res. 101, 35-41.

Jones et al. (1996) Environ. Entomol. 25, 481-487.

Keil and Ingraham, U.S. Pat. No. 2,521,582.

Kramm et al. (1982) J Invertebr Pathol 39, 1-5.

Matsunaga et al., U.S. Pat. No. 4,495,173.

Milner et al. (1966) Biocontrol Science and Technology 6, 3-9.

Osborne, L. S. (1990) Biological control of whiteflies and other pests with a fungal pathogen. In. U.S. Pat. No. 4,942,030.

Phillips, L. G., German, J. B., O'Neill, T. E., Foegeding, E. A., Harwalker, V. R., Kilara, A. (1990) Standardized procedure for measuring foaming properties of three proteins, a collaborative study. J. Food Sci. 55, 1441-1444, 1453.

Rodriguez Patino, J. M., Naranjo Delgado, M. D., and Linares Fernandez, J. A. (1995) Stability and mechanical strength of aqueous foams containing food proteins. Colloids and Surfaces A: Physicochemical and Engineering Aspects, 65-78.

Savolainen, U.S. Pat. No. 5,262,307.

Shimizu, S., and Yamaji, M. (2002) Pathogenicity of entomopathogenic fungi to the termite, *Reticulitermes speratus*. Jpn. J. Appl. Entomol. Zool. 46, 89-91.

Slattery, H., and Fitzgerald, R. J. (1998) Functional properties and bitterness of sodium caseinate hydrolysates prepared with a *Bacillus* proteinase. J. Food Sci., 418-422.

Stimac et al. U.S. Pat. No. 6,280,723.

Su, N.-Y., and Scheffrahn, R. H. (1986) A method to access, trap, and monitor field populations of the Formosan subterranean termite (Isoptera: Rhinotermitidae) in the urban environment. Sociobiology 12, 299-304.

Su, N.-Y., Scheffrahn, R. H., 1990. Economically important termites in the United States and their control. Sociobiol. 17, 77-94.

Su et al., 1996, Sociobiology 27: 253-275

Su et al., 1998, Pest Managem. Rev. 3: 1-13.

Vandenberg, J. D., Jackson, M. A., and Lacey, L. A. (1998) Relative efficacy of blastospores and aerial conidia of *Paecilomyces fumosoroseus* against the Russian Wheat Aphid. J. Invertebr. Pathol. 72, 181-183.

Vandenberg, J. D., Sandvol, L. E., Jaronski, S. T., Jackson, M. A., Souza, E. J., and Halbert, S. E. (2001) Efficacy of fungi for control of Russian wheat aphid (Homoptera: Aphididae) in irrigated wheat. Southwest. Entomol. 26, 73-85.

Vega, F. E., Jackson, M. A., and McGuire, M. R. (1999) Germination of conidia and blastospores of *Paecilomyces fumosoroseus* on the cuticle of the silverleaf whitefly, *Bemisia argentifolii*. Mycopathologia 147, 33-35.

Wells et al. (1995) J. Entomol. Sci. 30, 208-215.

Wright, M. S., Connick, J., William J., Jackson, M. A., (2003) Use of *Paeciomyces* spp. as pathogenic agents against subterranean termites. In U.S. Pat. No. 6,660,291.

We claim:

1. A composition for the control of insects comprising keratin hydrolysate and viable cells of a biological control agent comprising *Paecilomyces fumosoroseus* effective against at least one insect, in an insecticidally effective amount.

2. The composition of claim 1 wherein said composition is effective for forming a foam.

3. The composition of claim 1 wherein said insects are selected from the group consisting of termites, Japanese beetles, June beetles, vine weevils, banana weevils, and sugar beet root maggots.

4. The composition of claim 3 wherein said insects comprise termites and said biological control agent is effective against termites in a termiticidally effective amount.

5. The composition of claim 3 wherein said biological control agent further comprises *Metarhizium* species, *Beauveria* species, or *Verticilliuum* species.

6. The composition of claim 1 wherein said concentration of said cells is greater than or equal to about $1\times10^3$ cfu/ml and less than or equal to about $1\times10^{12}$ cfu/ml.

7. The composition of claim 1 wherein the concentration of said keratin hydrolysate is between about 0.1% and about 10%, by weight.

8. The composition of claim 4 wherein said keratin hydrolysate is in an amount effective to synergistically increase the termiticidal activity of said cells of *Paecilomyces fumosoroseus*.

9. The composition of claim 1 further comprising an inert carrier.

10. The composition of claim 9 wherein said inert carrier comprises water.

11. The composition of claim 1 wherein said keratin hydrolysate is substantially sterile.

12. The composition of claim 11 wherein said keratin hydrolysate has been treated effective to kill at least about 99.9% of any viable non-spore forming microorganisms therein.

13. The composition of claim 1 substantially free of antifungal or antimicrobial agents effective against said biological control agent.

14. The composition of claim 1 further comprising one or more adjuvants selected from the group consisting of foam stabilizers, foam viscosity modifiers, foam deliquescents, dispersants, humectants, nutrients for said biological control agent, antimicrobials which do not substantially inhibit the efficacy of said biological control agent as an insecticide, insecticidal agents, termite attractants, termite phagostimulants, termite aggregants, termite repellants, termite phagodeterrents, gases inhibitory to termites, gases beneficial to said biological control agent.

15. The composition of claim 1 wherein said cells comprise blastospores, conidia, mycelia or combinations thereof.

16. The composition of claim 14 wherein said cells comprise blastospores.

17. A method for the control of insects comprising applying to said insects, the locus of said insects, to material susceptible to infestation by said insects, or to the locus of material susceptible to infestation by said insects, a foam-forming composition comprising keratin hydrolysate and viable cells of a biological control agent comprising *Paecilomyces fumosoroseus* effective against at least one insect, in an insecticidally effective amount.

18. The method of claim 17 wherein said insects are selected from the group of soil-dwelling insects and termites.

19. The method of claim 18 wherein said insects are selected from the group consisting of termites, Japanese beetles, June beetles, vine weevils, banana weevils, and sugar beet root maggots.

20. The method of claim 17 wherein said insects comprise termites and said biological control agent is effective against termites in a termiticidally effective amount.

21. The method of claim 20 wherein said termites are of the family Rhinotermitidae.

22. The method of claim 21 wherein said termites comprise the Formosan subterranean termite, *Coptotermes formosanus*.

23. The method of claim 20 wherein said keratin hydrolysate is in an amount effective to synergistically increase the termiticidal activity of said cells of *Paecilomyces fumosoroseus*.

24. The method of claim 17 wherein said biological control agent further comprises *Metarhizium* species, *Beauveria* species, or *Verticilliuum* species.

25. The method of claim 17 wherein said concentration of said cells is greater than or equal to about $1\times10^3$ cfu/ml and less than or equal to about $1\times10^{12}$ cfu/ml.

26. The method of claim 17 wherein the concentration of said keratin hydrolysate is between about 0.1% and about 10%, by weight.

27. The method of claim 23 wherein the concentration of said keratin hydrolysate is between about 0.1% and about 10%, by weight.

28. The method of claim 17 wherein said composition further comprises an inert carrier.

29. The method of claim 28 wherein said inert carrier comprises water.

30. The method of claim 17 wherein said keratin hydrolysate is substantially sterile.

31. The method of claim 30 wherein said keratin hydrolysate has been treated effective to kill at least about 99.9% of any viable non-spore forming microorganisms therein.

32. The method of claim 17 wherein said composition is substantially free of antifungal or antimicrobial agents effective against said biological control agent.

33. The method of claim 17 wherein said composition further comprises one or more adjuvants selected from the group consisting of foam stabilizers, foam viscosity modifiers, foam deliquescents, dispersants, humectants, nutrients for said biological control agent, antimicrobials which do not substantially inhibit the efficacy of said biological control agent as an insecticide, insecticidal agents, termite attractants, termite phagostimulants, termite aggregants, termite repellants, termite phagodeterrents, gases inhibitory to termites, gases beneficial to said biological control agent.

34. The method of claim 17 wherein said cells comprise blastospores, conidia, mycelia, or combinations thereof.

35. The method of claim 34 wherein said cells comprise blastospores.

* * * * *